US006630138B2

(12) United States Patent
Gerlitz et al.

(10) Patent No.: US 6,630,138 B2
(45) Date of Patent: Oct. 7, 2003

(54) PROTEIN C DERIVATIVES

(75) Inventors: Bruce Edward Gerlitz, Indianapolis, IN (US); Brian William Grinnell, Indianapolis, IN (US); Bryan Edward Jones, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/182,263

(22) PCT Filed: Feb. 2, 2001

(86) PCT No.: PCT/US01/01221

§ 371 (c)(1), (2), (4) Date: Jul. 22, 2002

(87) PCT Pub. No.: WO01/59084

PCT Pub. Date: Aug. 16, 2001

(65) Prior Publication Data

US 2003/0022354 A1 Jan. 30, 2003

Related U.S. Application Data

(60) Provisional application No. 60/181,948, filed on Feb. 11, 2000, and provisional application No. 60/189,199, filed on Mar. 14, 2000.

(51) Int. Cl.$^7$ .......................... C12N 9/64; C12N 15/00; C12N 1/20; C07H 21/04; A61K 38/48

(52) U.S. Cl. ............................... 424/94.64; 435/320.1; 435/252.33; 435/226; 536/23.2

(58) Field of Search ............................. 435/226, 320.1, 435/252.33; 536/23.2; 424/94.64

(56) References Cited

U.S. PATENT DOCUMENTS

| | | | |
|---|---|---|---|
| 4,992,373 | A | 2/1991 | Bang et al. |
| 5,196,322 | A | 3/1993 | Bang et al. |
| 5,270,178 | A | 12/1993 | Gerlitz et al. |
| 5,358,932 | A | 10/1994 | Foster et al. |
| 5,453,373 | A | 9/1995 | Gerlitz et al. |
| 5,460,953 | A | 10/1995 | Gerlitz et al. |
| 5,837,843 | A | 11/1998 | Smirnov et al. |
| 5,847,085 | A | 12/1998 | Esmon et al. |
| 6,017,882 | A | 1/2000 | Nelsestuen |

FOREIGN PATENT DOCUMENTS

| | | | |
|---|---|---|---|
| EP | 0 296 413 | A2 | 9/1988 |
| EP | 0 354 504 | A2 | 5/1989 |
| EP | 0 443 874 | A2 | 2/1991 |
| JP | 03 072877 | A | 3/1991 |
| WO | WO 91/09960 | | 7/1991 |
| WO | WO 98/44000 | | 10/1998 |
| WO | WO 99/20767 | | 4/1999 |
| WO | WO 00/66753 | | 11/2000 |
| WO | WO 00/66754 | | 11/2000 |
| WO | WO 01/36462 | A2 | 5/2001 |
| WO | WO 01/57193 | | 8/2001 |
| WO | WO 01/59084 | A1 | 8/2001 |
| WO | WO 01/72328 | A2 | 10/2001 |
| WO | WO 01/72328 | A3 | 10/2001 |
| WO | WO 02/070681 | A1 | 9/2002 |

OTHER PUBLICATIONS

U.S. patent application Ser. No. 09/719,911, Gerlitz et al., filed Dec. 14, 2000.

U.S. patent application Ser. No. 10/129,893, Gerlitz et al., filed May 9, 2002.

U.S. patent application Ser. No. 10/168,407, Gerlitz et al., filed Jun. 20, 2002.

Kurz K., et al., Comparison in an Arteriovenous (AV) Shunt Model of Thrombosis in the Guinea Pig of the Antithrombotic and Anticoagulant Activities of a gla–domain Variant of Human Activated Protein C (APC) with Native APC and with a Low Molecular Weight Heparin (LMWH), Poster presentation at the 44$^{th}$ Annual Meeting of the American Society of Hematology (ASH) on Dec. 7, 2002, Philadelphia, PA.

U.S. patent application Ser. No. 09/497,591, Nelsestuen, filed Feb. 3, 2000.

U.S. patent application Ser. No. 09/803,810, Nelsestuen, filed Mar. 12, 2001.

Database Swall 'Online!, "Vitamin K–dependent protein C precursor" *European Bioinformatics Institute & Swiss Institute for Bioinformatics*, 1986.

Grinnell B, et al., "Glycosylation of Human protein C Affects Its Secretion, Processing, Functional Activities, and Activation by Thrombin", *Journal of Biological Chemistry*, vol. 266, No. 15, 1991, pp. 9778–9785.

Rezaie AR, et al., "Conversion of Glutamic Acid 192 to Glutamine in Activated Protein C Changes the Substrate Specificity and Increases Reactivity toward Macromolecular Inhibitors", *Journal of Biological Chemistry*, vol. 268, No. 27, 1993, pp. 19943–19948.

Mather T, et al., "The 2.8A crystal structure of Gla–domainless activated protein C", *The Embo Journal*, vol. 15, No. 24, 1996, pp. 6822–6831.

Tsiang M, et al., "Protein Engineering Thrombin for Optimal Specificity and Potency of Anticoagulant Activity in Vivo", *Biochemistry*, vol. 35, No. 51, 1996, pp. 16449–16457.

(List continued on next page.)

*Primary Examiner*—Rebecca E. Prouty
*Assistant Examiner*—Sheridan Swope
(74) *Attorney, Agent, or Firm*—Danica Hostettler; Lynn Apelgren

(57) ABSTRACT

Novel human protein C derivatives are described. These derivatives have increased anti-coagulation activity, resistance to serpin inactivation, and increased sensitivity to thrombin activation compared to wild-type protein C and retain the biological activity of the wild-type human protein C. These derivatives will require either less frequent administration and/or smaller dosage than wild-type human protein C in the treatment of acute coronary syndromes, vascular occlusive disorders, hypercoagulable states, thrombotic disorders and disease states predisposing to thrombosis.

18 Claims, No Drawings

OTHER PUBLICATIONS

Kurz K, et al., "Antithrombic Efficacy in the Guinea Pig of a Derivative of Human Protein C With Enhanced Activation by Thrombin", *Blood*, vol. 89, No. 2, 1997, pp. 534–540.

Shen L, et al., "Enhancing the Activity of Protein C by Mutagenesis To Improve the Membrane–Binding Site: Studies Related to Proline–10" *Biochemistry, American Chemical Society*, vol. 36, No. 51, 1997, pp. 16025–16031.

Shen L, et al., "Enhancement of Human Protein C Function by Site–directed Mutagenesis of the γ–Carboxyglutamic Acid Domain", *Journal of Biological Chemistry, American Society of Biological Chemists*, vol. 273, No. 47, 1998, pp. 31086–31091.

McDonald J, et al., "Comparison of Naturally Occuring Vitamin K–Dependent Proteins: Correlation of Amino Acid Sequences and Membrane Binding Properties Suggests a Membrane Contact Site", *Biochemistry*, vol. 36, No. 17, 1997, pp. 5120–5127.

Zhang L, et al., "The Contributions of Individual γ–Carboxyglutamic Acid Residues in the Calcium–dependent Binding of Recombinant Human Protein C to Acidic Phospholipid Vesicles", *The Journal of Biological Chemistry*, vol. 268, No. 16, 1993, pp. 12040–12045.

SEQUENCE LISTING

```
<160> NUMBER OF SEQ ID NOS: 12

<210> SEQ ID NO 1
<211> LENGTH: 419
<212> TYPE: PRT
<213> ORGANISM: Homo sapiens

<400> SEQUENCE: 1

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
            180                 185                 190
```

-continued

```
Lys Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro


<210> SEQ ID NO 2
<211> LENGTH: 461
<212> TYPE: PRT
<213> ORGANISM: Homo sapiens

<400> SEQUENCE: 2

Met Trp Gln Leu Thr Ser Leu Leu Leu Phe Val Ala Thr Trp Gly Ile
1               5                   10                  15

Ser Gly Thr Pro Ala Pro Leu Asp Ser Val Phe Ser Ser Ser Glu Arg
            20                  25                  30

Ala His Gln Val Leu Arg Ile Arg Lys Arg Ala Asn Ser Phe Leu Glu
        35                  40                  45

Glu Leu Arg His Ser Ser Leu Glu Arg Glu Cys Ile Glu Glu Ile Cys
    50                  55                  60

Asp Phe Glu Glu Ala Lys Glu Ile Phe Gln Asn Val Asp Asp Thr Leu
65                  70                  75                  80

Ala Phe Trp Ser Lys His Val Asp Gly Asp Gln Cys Leu Val Leu Pro
                85                  90                  95

Leu Glu His Pro Cys Ala Ser Leu Cys Cys Gly His Gly Thr Cys Ile
            100                 105                 110

Asp Gly Ile Gly Ser Phe Ser Cys Asp Cys Arg Ser Gly Trp Glu Gly
        115                 120                 125

Arg Phe Cys Gln Arg Glu Val Ser Phe Leu Asn Cys Ser Leu Asp Asn
    130                 135                 140
```

-continued

```
Gly Gly Cys Thr His Tyr Cys Leu Glu Glu Val Gly Trp Arg Arg Cys
145                 150                 155                 160

Ser Cys Ala Pro Gly Tyr Lys Leu Gly Asp Asp Leu Leu Gln Cys His
                165                 170                 175

Pro Ala Val Lys Phe Pro Cys Gly Arg Pro Trp Lys Arg Met Glu Lys
            180                 185                 190

Lys Arg Ser His Leu Lys Arg Asp Thr Glu Asp Gln Glu Asp Gln Val
        195                 200                 205

Asp Pro Arg Leu Ile Asp Gly Lys Met Thr Arg Arg Gly Asp Ser Pro
    210                 215                 220

Trp Gln Val Val Leu Leu Asp Ser Lys Lys Lys Leu Ala Cys Gly Ala
225                 230                 235                 240

Val Leu Ile His Pro Ser Trp Val Leu Thr Ala Ala His Cys Met Asp
                245                 250                 255

Glu Ser Lys Lys Leu Leu Val Arg Leu Gly Glu Tyr Asp Leu Arg Arg
            260                 265                 270

Trp Glu Lys Trp Glu Leu Asp Leu Asp Ile Lys Glu Val Phe Val His
        275                 280                 285

Pro Asn Tyr Ser Lys Ser Thr Thr Asp Asn Asp Ile Ala Leu Leu His
    290                 295                 300

Leu Ala Gln Pro Ala Thr Leu Ser Gln Thr Ile Val Pro Ile Cys Leu
305                 310                 315                 320

Pro Asp Ser Gly Leu Ala Glu Arg Glu Leu Asn Gln Ala Gly Gln Glu
                325                 330                 335

Thr Leu Val Thr Gly Trp Gly Tyr His Ser Ser Arg Glu Lys Glu Ala
            340                 345                 350

Lys Arg Asn Arg Thr Phe Val Leu Asn Phe Ile Lys Ile Pro Val Val
        355                 360                 365

Pro His Asn Glu Cys Ser Glu Val Met Ser Asn Met Val Ser Glu Asn
    370                 375                 380

Met Leu Cys Ala Gly Ile Leu Gly Asp Arg Gln Asp Ala Cys Glu Gly
385                 390                 395                 400

Asp Ser Gly Gly Pro Met Val Ala Ser Phe His Gly Thr Trp Phe Leu
                405                 410                 415

Val Gly Leu Val Ser Trp Gly Glu Gly Cys Gly Leu Leu His Asn Tyr
            420                 425                 430

Gly Val Tyr Thr Lys Val Ser Arg Tyr Leu Asp Trp Ile His Gly His
        435                 440                 445

Ile Arg Asp Lys Glu Ala Pro Gln Lys Ser Trp Ala Pro
    450                 455                 460


<210> SEQ ID NO 3
<211> LENGTH: 419
<212> TYPE: PRT
<213> ORGANISM: Homo sapiens

<400> SEQUENCE: 3

Ala Asn Ser Phe Leu Glu Glu Leu Arg His Gly Ser Leu Glu Arg Glu
1               5                   10                  15

Cys Ile Glu Glu Ile Cys Asp Phe Glu Glu Ala Lys Glu Ile Phe Glu
            20                  25                  30

Asp Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60
```

-continued

```
Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Phe Pro Arg Leu Ile Lys Gly Lys Met Thr
                165                 170                 175

Arg Arg Gly Asp Ser Pro Trp Gln Val Val Leu Leu Asp Ser Lys Lys
            180                 185                 190

Lys Ser Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro


<210> SEQ ID NO 4
<211> LENGTH: 419
<212> TYPE: PRT
<213> ORGANISM: Homo sapiens

<400> SEQUENCE: 4

Ala Asn Ser Phe Leu Glu Glu Leu Arg His Gly Ser Leu Glu Arg Glu
1               5                   10                  15
```

-continued

```
Cys Ile Glu Glu Ile Cys Asp Phe Glu Glu Ala Lys Glu Ile Phe Glu
            20                  25                  30

Asp Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Phe Pro Arg Leu Ile Lys Gly Lys Met Thr
                165                 170                 175

Arg Arg Gly Asp Ser Pro Trp Gln Val Val Leu Leu Asp Ser Lys Lys
            180                 185                 190

Lys Ser Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Ser Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro
```

-continued

<210> SEQ ID NO 5
<211> LENGTH: 419
<212> TYPE: PRT
<213> ORGANISM: Homo sapiens

<400> SEQUENCE: 5

```
Ala Asn Ser Phe Leu Glu Glu Leu Arg His Gly Ser Leu Glu Arg Glu
1               5                   10                  15

Cys Ile Glu Glu Ile Cys Asp Phe Glu Glu Ala Lys Glu Ile Phe Glu
            20                  25                  30

Asp Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Phe Pro Arg Leu Ile Lys Gly Lys Met Thr
                165                 170                 175

Arg Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335

Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380
```

-continued

```
Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro


<210> SEQ ID NO 6
<211> LENGTH: 419
<212> TYPE: PRT
<213> ORGANISM: Homo sapiens

<400> SEQUENCE: 6

Ala Asn Ser Phe Leu Glu Glu Leu Arg Gln Gly Ser Leu Glu Arg Glu
1               5                   10                  15

Cys Ile Glu Glu Ile Cys Asp Phe Glu Glu Ala Lys Glu Ile Phe Glu
            20                  25                  30

Asp Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Phe Pro Arg Leu Ile Lys Gly Lys Met Thr
                165                 170                 175

Arg Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285

Asn Gln Ala Gly Gln Glu Thr Leu Val Thr Gly Trp Gly Tyr His Ser
    290                 295                 300

Ser Arg Glu Lys Glu Ala Lys Arg Asn Arg Thr Phe Val Leu Asn Phe
305                 310                 315                 320

Ile Lys Ile Pro Val Val Pro His Asn Glu Cys Ser Glu Val Met Ser
                325                 330                 335
```

-continued

```
Asn Met Val Ser Glu Asn Met Leu Cys Ala Gly Ile Leu Gly Asp Arg
            340                 345                 350

Gln Asp Ala Cys Glu Gly Asp Ser Gly Gly Pro Met Val Ala Ser Phe
        355                 360                 365

His Gly Thr Trp Phe Leu Val Gly Leu Val Ser Trp Gly Glu Gly Cys
    370                 375                 380

Gly Leu Leu His Asn Tyr Gly Val Tyr Thr Lys Val Ser Arg Tyr Leu
385                 390                 395                 400

Asp Trp Ile His Gly His Ile Arg Asp Lys Glu Ala Pro Gln Lys Ser
                405                 410                 415

Trp Ala Pro


<210> SEQ ID NO 7
<211> LENGTH: 1260
<212> TYPE: DNA
<213> ORGANISM: Homo sapiens

<400> SEQUENCE: 7

gccaactcct tcctggagga gctccgtcac agcagcctgg agcgggagtg catagaggag     60

atctgtgact tcgaggaggc caaggaaatt ttccaaaatg tggatgacac actggccttc    120

tggtccaagc acgtcgacgg tgaccagtgc ttggtcttgc ccttggagca cccgtgcgcc    180

agcctgtgct gcgggcacgg cacgtgcatc gacggcatcg gcagcttcag ctgcgactgc    240

cgcagcggct gggagggccg cttctgccag cgcgaggtga gcttcctcaa ttgctcgctg    300

gacaacggcg gctgcacgca ttactgccta gaggaggtgg gctggcggcg ctgtagctgt    360

gcgcctggct acaagctggg ggacgacctc ctgcagtgtc accccgcagt gaagttccct    420

tgtgggaggc cctggaagcg gatggagaag aagcgcagtc acctgaaacg agacacagaa    480

gaccaagaag accaagtaga tccgcggctc attgatggga agatgaccag gcggggagac    540

agcccctggc aggtggtcct gctggactca aagaagaagc tggcctgcgg ggcagtgctc    600

atccacccct cctgggtgct gacagcggcc cactgcatgg atgagtccaa gaagctcctt    660

gtcaggcttg gagagtatga cctgcggcgc tgggagaagt gggagctgga cctggacatc    720

aaggaggtct tcgtccaccc caactacagc aagagcacca ccgacaatga catcgcactg    780

ctgcacctgg cccagcccgc caccctctcg cagaccatag tgcccatctg cctcccggac    840

agcggccttg cagagcgcga gctcaatcag gccggccagg agaccctcgt gacgggctgg    900

ggctaccaca gcagccgaga gaaggaggcc aagagaaacc gcaccttcgt cctcaacttc    960

atcaagattc ccgtggtccc gcacaatgag tgcagcgagg tcatgagcaa catggtgtct   1020

gagaacatgc tgtgtgcggg catcctcggg gaccggcagg atgcctgcga gggcgacagt   1080

gggggggccca tggtcgcctc cttccacggc acctggttcc tggtgggcct ggtgagctgg   1140

ggtgagggct gtgggctcct tcacaactac ggcgtttaca ccaaagtcag ccgctacctc   1200

gactggatcc atgggcacat cagagacaag gaagcccccc agaagagctg ggcaccttag   1260


<210> SEQ ID NO 8
<211> LENGTH: 1386
<212> TYPE: DNA
<213> ORGANISM: Homo sapiens

<400> SEQUENCE: 8

atgtggcagc tcacaagcct cctgctgttc gtggccacct ggggaatttc cggcacacca     60

gctcctcttg actcagtgtt ctccagcagc gagcgtgccc accaggtgct gcggatccgc    120
```

-continued

```
aaacgtgcca actccttcct ggaggagctc cgtcacagca gcctggagcg ggagtgcata    180

gaggagatct gtgacttcga ggaggccaag gaaattttcc aaaatgtgga tgacacactg    240

gccttctggt ccaagcacgt cgacggtgac cagtgcttgg tcttgccctt ggagcacccg    300

tgcgccagcc tgtgctgcgg gcacggcacg tgcatcgacg gcatcggcag cttcagctgc    360

gactgccgca gcggctggga gggccgcttc tgccagcgcg aggtgagctt cctcaattgc    420

tcgctggaca acggcggctg cacgcattac tgcctagagg aggtgggctg gcggcgctgt    480

agctgtgcgc ctggctacaa gctgggggac gacctcctgc agtgtcaccc cgcagtgaag    540

ttcccttgtg ggaggccctg gaagcggatg gagaagaagc gcagtcacct gaaacgagac    600

acagaagacc aagaagacca agtagatccg cggctcattg atgggaagat gaccaggcgg    660

ggagacagcc cctggcaggt ggtcctgctg gactcaaaga agaagctggc ctgcggggca    720

gtgctcatcc acccctcctg ggtgctgaca gcggcccact gcatggatga gtccaagaag    780

ctccttgtca ggcttggaga gtatgacctg cggcgctggg agaagtggga gctggacctg    840

gacatcaagg aggtcttcgt ccaccccaac tacagcaaga gcaccaccga caatgacatc    900

gcactgctgc acctggccca gcccgccacc ctctcgcaga ccatagtgcc catctgcctc    960

ccggacagcg gccttgcaga gcgcgagctc aatcaggccg gccaggagac cctcgtgacg   1020

ggctggggct accacagcag ccgagagaag gaggccaaga gaaaccgcac cttcgtcctc   1080

aacttcatca agattcccgt ggtcccgcac aatgagtgca gcgaggtcat gagcaacatg   1140

gtgtctgaga acatgctgtg tgcgggcatc ctcggggacc ggcaggatgc ctgcgagggc   1200

gacagtgggg ggcccatggt cgcctccttc cacggcacct ggttcctggt gggcctggtg   1260

agctggggtg agggctgtgg gctccttcac aactacggcg tttacaccaa agtcagccgc   1320

tacctcgact ggatccatgg gcacatcaga gacaaggaag ccccccagaa gagctgggca   1380

ccttag                                                              1386
```

<210> SEQ ID NO 9
<211> LENGTH: 1386
<212> TYPE: DNA
<213> ORGANISM: Homo sapiens

<400> SEQUENCE: 9

```
atgtggcagc tcacaagcct cctgctgttc gtggccacct ggggaatttc cggcacacca     60

gctcctcttg actcagtgtt ctccagcagc gagcgtgccc accaggtgct gcggatccgc    120

aaacgtgcca actccttcct ggaggagctc cgtcacggga gcctggagcg ggagtgcata    180

gaggagatct gtgacttcga ggaggccaag gaaattttcg aagatgtgga tgacacactg    240

gccttctggt ccaagcacgt cgacggtgac cagtgcttgg tcttgccctt ggagcacccg    300

tgcgccagcc tgtgctgcgg gcacggcacg tgcatcgacg gcatcggcag cttcagctgc    360

gactgccgca gcggctggga gggccgcttc tgccagcgcg aggtgagctt cctcaattgc    420

tctctggaca acggcggctg cacgcattac tgcctagagg aggtgggctg gcggcgctgt    480

agctgtgcgc ctggctacaa gctgggggac gacctcctgc agtgtcaccc cgcagtgaag    540

ttcccttgtg ggaggccctg gaagcggatg gagaagaagc gcagtcacct gaaacgagac    600

acagaagacc aagaagacca agtattcccg cggctcatta aggggaagat gaccaggcgg    660

ggagacagcc cctggcaggt ggtcctgctg gactcaaaga agaagtccgc ctgcggggca    720

gtgctcatcc acccctcctg ggtgctgaca gcggcccact gcatggatga gtccaagaag    780

ctccttgtca ggcttggaga gtatgacctg cggcgctggg agaagtggga gctggacctg    840
```

-continued

```
gacatcaagg aggtcttcgt ccacccccaac tacagcaaga gcaccaccga caatgacatc    900

gcactgctgc acctggccca gcccgccacc ctctcgcaga ccatagtgcc catctgcctc    960

ccggacagcg gccttgcaga gcgcgagctc aatcaggccg gccaggagac cctcgtgacg   1020

ggctggggct accacagcag ccgagagaag gaggccaaga gaaaccgcac cttcgtcctc   1080

aacttcatca agattcccgt ggtcccgcac aatgagtgca gcgaggtcat gagcaacatg   1140

gtgtctgaga acatgctgtg tgcgggcatc ctcggggacc ggcaggatgc ctgcgagggc   1200

gacagtgggg ggcccatggt cgcctccttc cacggcacct ggttcctggt gggcctggtg   1260

agctggggtg agggctgtgg gctccttcac aactacggcg tttacaccaa agtcagccgc   1320

tacctcgact ggatccatgg gcacatcaga gacaaggaag ccccccagaa gagctgggca   1380

ccttag                                                              1386


<210> SEQ ID NO 10
<211> LENGTH: 1386
<212> TYPE: DNA
<213> ORGANISM: Homo sapiens

<400> SEQUENCE: 10

atgtggcagc tcacaagcct cctgctgttc gtggccacct ggggaatttc cggcacacca     60

gctcctcttg actcagtgtt ctccagcagc gagcgtgccc accaggtgct gcggatccgc    120

aaacgtgcca actccttcct ggaggagctc cgtcacggga gcctggagcg ggagtgcata    180

gaggagatct gtgacttcga ggaggccaag gaaattttcg aagatgtgga tgacacactg    240

gccttctggt ccaagcacgt cgacggtgac cagtgcttgg tcttgccctt ggagcacccg    300

tgcgccagcc tgtgctgcgg gcacggcacg tgcatcgacg gcatcggcag cttcagctgc    360

gactgccgca gcggctggga gggccgcttc tgccagcgcg aggtgagctt cctcaattgc    420

tctctggaca acggcggctg cacgcattac tgcctagagg aggtgggctg gcggcgctgt    480

agctgtgcgc ctggctacaa gctgggggac gacctcctgc agtgtcaccc cgcagtgaag    540

ttcccttgtg ggaggccctg gaagcggatg gagaagaagc gcagtcacct gaaacgagac    600

acagaagacc aagaagacca agtattcccg cggctcatta aggggaagat gaccaggcgg    660

ggagacagcc cctggcaggt ggtcctgctg gactcaaaga agaagtccgc ctgcggggca    720

gtgctcatcc acccctcctg ggtgctgaca gcggcccact gcatggatga gtccaagaag    780

ctccttgtca ggcttggaga gtatgacctg cggcgctggg agaagtggga gctggacctg    840

gacatcaagg aggtcttcgt ccacccccaac tacagcaaga gcaccagcga caatgacatc    900

gcactgctgc acctggccca gcccgccacc ctctcgcaga ccatagtgcc catctgcctc    960

ccggacagcg gccttgcaga gcgcgagctc aatcaggccg gccaggagac cctcgtgacg   1020

ggctggggct accacagcag ccgagagaag gaggccaaga gaaaccgcac cttcgtcctc   1080

aacttcatca agattcccgt ggtcccgcac aatgagtgca gcgaggtcat gagcaacatg   1140

gtgtctgaga acatgctgtg tgcgggcatc ctcggggacc ggcaggatgc ctgcgagggc   1200

gacagtgggg ggcccatggt cgcctccttc cacggcacct ggttcctggt gggcctggtg   1260

agctggggtg agggctgtgg gctccttcac aactacggcg tttacaccaa agtcagccgc   1320

tacctcgact ggatccatgg gcacatcaga gacaaggaag ccccccagaa gagctgggca   1380

ccttag                                                              1386
```

-continued

<210> SEQ ID NO 11
<211> LENGTH: 1386
<212> TYPE: DNA
<213> ORGANISM: Homo sapiens

<400> SEQUENCE: 11
atgtggcagc tcacaagcct cctgctgttc gtggccacct ggggaatttc cggcacacca 60
gctcctcttg actcagtgtt ctccagcagc gagcgtgccc accaggtgct gcggatccgc 120
aaacgtgcca actccttcct ggaggagctc cgtcaaggga gcctggagcg ggagtgcata 180
gaggagatct gtgacttcga ggaggccaag gaaattttcg aagatgtgga tgacacactg 240
gccttctggt ccaagcacgt cgacggtgac cagtgcttgg tcttgccctt ggagcacccg 300
tgcgccagcc tgtgctgcgg gcacggcacg tgcatcgacg gcatcggcag cttcagctgc 360
gactgccgca gcggctggga gggccgcttc tgccagcgcg aggtgagctt cctcaattgc 420
tctctggaca acggcggctg cacgcattac tgcctagagg aggtgggctg gcggcgctgt 480
agctgtgcgc ctggctacaa gctgggggac gacctcctgc agtgtcaccc cgcagtgaag 540
ttcccttgtg ggaggccctg gaagcggatg gagaagaagc gcagtcacct gaaacgagac 600
acagaagacc aagaagacca agtattcccg cggctcatta aggggaagat gaccaggcgg 660
ggagacagcc cctggcaggt ggtcctgctg gactcaaaga agaagctggc ctgcggggca 720
gtgctcatcc acccctcctg ggtgctgaca gcggcccact gcatggatga gtccaagaag 780
ctccttgtca ggcttggaga gtatgacctg cggcgctggg agaagtggga gctggacctg 840
gacatcaagg aggtcttcgt ccaccccaac tacagcaaga gcaccaccga caatgacatc 900
gcactgctgc acctggccca gcccgccacc ctctcgcaga ccatagtgcc catctgcctc 960
ccggacagcg gccttgcaga gcgcgagctc aatcaggccg gccaggagac cctcgtgacg 1020
ggctggggct accacagcag ccgagagaag gaggccaaga gaaaccgcac cttcgtcctc 1080
aacttcatca agattcccgt ggtcccgcac aatgagtgca gcgaggtcat gagcaacatg 1140
gtgtctgaga acatgctgtg tgcgggcatc ctcggggacc ggcaggatgc ctgcgagggc 1200
gacagtgggg ggcccatggt cgcctccttc cacggcacct ggttcctggt gggcctggtg 1260
agctggggtg agggctgtgg gctccttcac aactacggcg tttacaccaa agtcagccgc 1320
tacctcgact ggatccatgg gcacatcaga gacaaggaag ccccccagaa gagctgggca 1380
ccttag 1386

<210> SEQ ID NO 12
<211> LENGTH: 1386
<212> TYPE: DNA
<213> ORGANISM: Homo sapiens

<400> SEQUENCE: 12
atgtggcagc tcacaagcct cctgctgttc gtggccacct ggggaatttc cggcacacca 60
gctcctcttg actcagtgtt ctccagcagc gagcgtgccc accaggtgct gcggatccgc 120
aaacgtgcca actccttcct ggaggagctc cgtcaaggga gcctggagcg ggagtgcata 180
gaggagatct gtgacttcga ggaggccaag gaaattttcg aagatgtgga tgacacactg 240
gccttctggt ccaagcacgt cgacggtgac cagtgcttgg tcttgccctt ggagcacccg 300
tgcgccagcc tgtgctgcgg gcacggcacg tgcatcgacg gcatcggcag cttcagctgc 360
gactgccgca gcggctggga gggccgcttc tgccagcgcg aggtgagctt cctcaattgc 420
tctctggaca acggcggctg cacgcattac tgcctagagg aggtgggctg gcggcgctgt 480

-continued

```
agctgtgcgc ctggctacaa gctgggggac gacctcctgc agtgtcaccc cgcagtgaag    540

ttcccttgtg ggaggccctg gaagcggatg gagaagaagc gcagtcacct gaaacgagac    600

acagaagacc aagaagacca agtattcccg cggctcatta aggggaagat gaccaggcgg    660

ggagacagcc cctggcaggt ggtcctgctg gactcaaaga agaagctggc ctgcggggca    720

gtgctcatcc acccctcctg ggtgctgaca gcggcccact gcatggatga gtccaagaag    780

ctccttgtca ggcttggaga gtatgacctg cggcgctggg agaagtggga gctggacctg    840

gacatcaagg aggtcttcgt ccaccccaac tacagcaaga gcaccaccga caatgacatc    900

gcactgctgc acctggccca gcccgccacc ctctcgcaga ccatagtgcc catctgcctc    960

ccggacagcg gccttgcaga gcgcgagctc aatcaggccg gccaggagac cctcgtgacg   1020

ggctggggct accacagcag ccgagagaag gaggccaaga gaaaccgcac cttcgtcctc   1080

aacttcatca agattcccgt ggtcccgcac aatgagtgca gcgaggtcat gagcaacatg   1140

gtgtctgaga acatgctgtg tgcgggcatc ctcggggacc ggcaggatgc ctgcgagggc   1200

gacagtgggg ggcccatggt cgcctccttc cacggcacct ggttcctggt gggcctggtg   1260

agctggggtg agggctgtgg gctccttcac aactacggcg tttacaccaa agtcagccgc   1320

tacctcgact ggatccatgg gcacatcaga gacaaggaag ccccccagaa gagctgggca   1380

ccttag                                                              1386
```

PROTEIN C DERIVATIVES

This application is a 35 U.S.C. 371 filing of PCT/US01/01221 filed Feb. 2, 2001, now WO 01/59084 published Aug. 16, 2001, which claims benefit of No. 60/181,948 filed Feb. 11, 2000 and No. 60/189,199 filed Mar. 14, 2000.

This invention relates to novel polynucleotides, polypeptides encoded by them and to the use of such polynuoleotides and polypeptides. More specifically, the invention relates to human protein C derivatives with increased anti-coagulant activity, resistance to serpin inactivation, increased sensitivity to thrombin activation, or a combination thereof, when compared to wild-type activated protein C; to their production, and to pharmaceutical compositions comprising these human protein C derivatives.

Protein C is a serine protease and naturally occurring anti-coagulant that plays a role in the regulation of hemostasis by inactivating Factors $V_a$ and $VIII_a$ in the coagulation cascade. Human protein C is made in vivo as a single polypeptide of 461 amino acid a. This polypeptide undergoes multiple post-translational modifications including, 1) cleavage of a 42 amino acid signal sequence; 2) cleavage of lysine and arginine residues (positions 156 and 157) to make a 2-chain inactive precursor or zymogen (a 155 amino acid residue light chain attached via a disulfide bridge to a 262 amino acid residue heavy chain); 3) vitamin K-dependent carboxylation of nine glutamic acid residues located within the amino-terminal 45 residues (gla-domain): and, 4) carbohydrate attachment at four sites (one in the light chain and three in the heavy chain). Finally, the 2-chain zymogen may be activated by removal of a dodecapeptide at the N-terminus of the heavy chain, producing activated protein C (aPC) possessing greater enzymatic activity than the 2-chain zymogen.

Blood coagulation is a highly complex process regulated by the balance between pro-coagulant and anti-coagulant mechanisms. This balance determines a condition of either normal hemostasis or abnormal pathological thrombus generation and the progression, for example, of coronary thrombosis leading to acute coronary syndromes (ACS; e.g. unstable angina, myocardial infarction). Two major factors control this balance; the generation of fibrin and the activation and subsequent aggregation of platelets. Both processes are controlled by the generation of the enzyme thrombin, which occurs following activation of the clotting cascade. Thrombin, in complex with thrombomodulin, also functions as a potent anti-coagulant since it activates protein C zymogen to aPC, which in turn inhibits the generation of thrombin. Thus, through the feedback regulation of thrombin generation via the inactivation of Factors Va and VIIIa, aPC functions as perhaps the most important down-regulator of blood coagulation resulting in protection against thrombosis. In addition, aPC has anti-inflammatory properties, and exerts profibrinolytic effects that facilitate clot lysis.

Various methods of obtaining protein C from plasma and producing protein C, aPC and protein C/aPC polypeptides through recombinant DNA technology are known in the art and have been described. See e.g., U.S. Pat. Nos. 4,775,624 and 5,358,932. Despite improvements in methods to produce aPC through recombinant DNA technology, aPC and derivatives thereof are difficult and costly to produce.

Unlike the zymogen protein C, activated protein C has an extremely short half-life. A major reason for the short half-life is that blood levels of aPC are regulated by molecules known as serpins (Serine Protease Inhibitors), which covalently bind to aPC forming an inactive serpin/aPC complex. The serpin/aPC complexes are formed when aPC binds and proteolytically cleaves a reactive site loop within the serpin; upon cleavage, the serpin undergoes a conformational change irreversibly inactivating aPC. The serpin/aPC complex is then eliminated from the bloodstream via hepatic receptors for the serpin/aPC complex. As a result, aPC has a relatively short half-life compared to the zymogen; approximately 20 minutes for aPC versus approximately 10 hours for human protein C zymogen (Okajima, et al., *Thromb Haemost* 63(1):48–53, 1990).

Therefore, an aPC derivative exhibiting resistance to serpin inactivation, while maintaining the desirable biological activities of aPC (e.g., anticoagulant, fibrinolytic, and anti-inflammatory activities), provides a compound that has an increased plasma half-life and is effectively more potent than the parent compound, requiring substantially reduced dosage levels for therapeutic applications. The potency advantages are especially important in disease states in which serpin levels are elevated.

Additionally, an aPC derivative exhibiting increased anti-coagulant activity, while maintaining the other biological activities of aPC (e.g., fibrinolytic, and anti-inflammatory activities), provides a compound that is effectively more potent than the parent compound, requiring substantially reduced dosage levels for therapeutic applications.

Enhancement of human protein C calcium and membrane binding activity by site-directed mutagenesis of the gla-domain has been reported by several investigator a, for example, Shen et al. (*J Biol. Chem.,* 273(47) 31086–91, 1998.) and Shen et al. (*Biochemistry,* 36(51) 16025–31, 1997). Through continued scientific experiments, analysis, and innovation, the present inventors identified specific sites and modified targeted amino acid residues in the gla-domain of the aPC molecule. Surprisingly, we found increased anti-coagulant activity of the aPC derivative when specific amino acid substitutions were performed. Therefore, an aPC derivative exhibiting increased anti-coagulant activity, while maintaining the other biological activities of aPC (e.g., fibrinolytic, and anti-inflammatory activities), provides a compound that is effectively more potent than the parent compound, requiring substantially reduced dosage levels for therapeutic applications.

Furthermore, human protein C derivatives with increased sensitivity to thrombin activation (hyper-activatable zymogens) are useful as site-activated anti-thrombotic agents, as described, for example, in U.S. Pat. No. 5,453,373 and in Richardson et al. (*Protein Science,* 3:711–712, 1994). Such hyper-activatable zymogens can also be constructed to contain the gla-domain mutants and the serpin resistant derivatives described above. These derivatives have increased anti-coagulant activity, resistance to serpin inactivation, and increased sensitivity to thrombin activation when compared to wild-type human protein C.

Accordingly, the present invention describes novel human protein C derivatives. These human protein C derivatives retain the important biological activity when compared to wild-type protein C and have increased anti-coagulant activity, resistance to serpin inactivation, and increased sensitivity to thrombin activation when compared to wild-type human protein C. Other protein C derivatives of the present invention have increased sensitivity to thrombin activation and increased anti-coagulant activity or increased sensitivity to thrombin activation and resistance to serpin inactivation.

Therefore, these compounds provide various advantages, for example, site-activation, less frequent administration and/or smaller dosages and thus a reduction in the overall cost of production of the therapy. Thus, these compounds exhibit an advantage over current therapy in disease states of acute coronary syndromes such as unstable angina or myocardial infarction.

The present invention provides a human protein C derivative comprising SEQ ID NO: 1 wherein Asp at position 167 is substituted with Phe; Asp at position 172 is substituted with Lys and further comprising at least one amino acid substitution selected from the group consisting of:

His at position 10, Ser at position 11, or Ser at position 12 are independently substituted with any amino acid; Gln at position 32 is substituted with Glu; Asn at position 33 is substituted with Asp or Phe; and, amino acids at positions 194, 195, 228, 249, 254, 302, or 316 are substituted with an amino acid selected from Ser, Ala, Thr, His, Leu, Lys, Arg, Asn, Asp, Glu, Gly, and Gln.

The present invention also provides recombinant DNA molecules encoding the human protein C derivatives of the present invention, in particular those comprising SEQ ID Nos: 9, 10, 11, and 12.

Another aspect of the present invention provides protein sequences of these same human protein C derivatives, particularly those comprising SEQ ID NOS: 3, 4, 5, and 6, and the activated forms thereof.

The present invention comprises methods of treating acute coronary syndromes such as myocardial infarction and unstable angina.

The present invention further comprises methods of treating thrombotic disorders. Such disorders include, but are not limited to, stroke, abrupt closure following angioplasty or stent placement, and thrombosis as a result of peripheral vascular surgery.

The present invention comprises methods of treating vascular occlusive disorders and hypercoagulable states including: sepsis, disseminated intravascular coagulation, purpura fulminans, major trauma, major surgery, burns, adult respiratory distress syndrome, transplantations, deep vein thrombosis, heparin-induced thrombocytopenia, sickle cell disease, thalassemia, viral hemorrhagic fever, thrombotic thrombocytopenic purpura, and hemolytic uremic syndrome.

Another aspect of the invention comprises treating the diseases and conditions caused by or resulting from protein C deficiency as defined herein.

Another embodiment of the present invention is a method of treating sepsis comprising the administration to a patient in need thereof, a pharmaceutically effective amount of a human protein C derivative of this invention in combination with bacterial permeability increasing protein.

Another embodiment of the present invention is a method of treating thrombotic disorders which comprises: administering to a patient in need thereof a pharmaceutically effective amount of a human protein C derivative of this invention in combination with an anti-platelent agent.

The present invention further provides a method of treating acute arterial thrombotic occlusion, thromboembolism, or stenosis in coronary, cerebral or peripheral arteries or in vascular grafts which comprises administering to a patient in need thereof a pharmaceutically effective amount of a human activated protein C in combination with a thrombolytic agent.

The present invention further provides a method of treating human patients with genetically predisposed prothrombotic disorders, for example, protein C deficiency, Factor V Leiden mutation, and prothrombin gene G20210A mutation, which comprises administering gene therapy to said patients with a recombinant DNA molecule encoding a protein C derivative.

The present invention also provides a pharmaceutical composition comprising a pharmaceutically acceptable carrier or diluent and a human protein C derivative of this invention.

Methods and aspects of producing the novel isolated human protein C derivatives are also an aspect of this invention.

The present invention also provides for the use of the human activated protein C derivatives of this invention for the manufacture of a medicament for the treatment of the above-mentioned indications Methods and aspects of producing the novel human protein derivatives are also an aspect of this invention.

For purposes of the present invention, as disclosed and claimed herein, the following terms are as defined below.

Anti-platelet agent—one or more agents alone or in combination which reduces the ability of platelets to aggregate. Agents understood and appreciated in the art include those cited in, for example, Remington, *The Science and Practice of Pharmacy*, Nineteenth Edition, Vol II, pages 924–25, Mack Publishing Co., herein incorporated by reference. Such agents include but are not limited to aspirin (ASA), clopidogrel, ReoPro® (abciximab), dipyridamole, ticlopidine and IIb/IIIa antagonists.

Zymogen—protein C zymogen, as used herein, refers to secreted, inactive forms, whether one chain or two chains of protein C or derivatives thereof. Cleavage of lysine and arginine residues (positions 156 and 157) results in a 2-chain (heavy and light) inactive zymogen.

Activated protein C refers to the activated form of protein C zymogen which is produced after by removal of a dodecapeptide at the N-terminus of the heavy chain, producing activated protein C.

Activated protein C or aPC refers to recombinant aPC. aPC includes and is preferably recombinant human aPC although aPC may also include other species having protein C proteolytic, amidolytic, esterolytic, and biological (anti-coagulant, anti-inflammatory, or pro-fibrinolytic) activities.

Human protein C derivative(s) refers to the recombinantly produced derivatives of this invention that differ from wild-type human protein C but when activated retain the essential properties i.e., proteolytic, amidolytic, esterolytic, and biological (anti-coagulant, anti-inflammatory, pro-fibrinolytic activities). The definition of human protein C derivatives as used herein also includes the activated form of the above-identified human protein C derivatives.

Treating—describes the management and care of a patient for the purpose of combating a disease, condition, or disorder whether to eliminate the disease, condition, or disorder, or prophylactically to prevent the onset of the symptoms or complications of the disease, condition, or disorder.

Continuous infusion—continuing substantially uninterrupted the introduction of a solution or suspension into a vein for a specified period of time.

Bolus injection—the injection of a drug in a defined quantity (called a bolus) over a period of time up to about 120 minutes.

Suitable for administration—a lyophilized formulation or solution that is appropriate to be given as a therapeutic agent.

Unit dosage form—refers to physically discrete units suitable as unitary dosages for human subjects, each unit containing a predetermined quantity of active material calculated to produce the desired therapeutic effect, in association with a suitable pharmaceutical excipient.

Hypercoagulable states—excessive coagulability associated with disseminated intravascular coagulation, prethrombotic conditions, activation of coagulation, or congenital or acquired deficiency of clotting factors such as aPC.

Protein C deficiency—protein C deficiency as used herein can be congenital or acquired. For either type, the protein C level in circulation is below the lower limit of the normal range. Skilled artisans realize that the normal range is established by a standard protocol utilizing FDA approved equipment and diagnostic kits for determining protein C levels.

Pharmaceutically effective amount—a therapeutically efficacious amount of a pharmaceutical compound. The particular dose of the compound administered according to this invention will, of course, be determined by the attending physician evaluating the particular circumstances surrounding the case, including the compound administered, the particular condition being treated, the patient characteristics and similar considerations.

Acute coronary syndromes—clinical manifestations of coronary atherosclerosis complicated by coronary plaque rupture, superimposed coronary thrombosis, and jeopardized coronary blood flow resulting in coronary ischemia and/or myocardial infarction. The spectrum of acute coronary syndromes includes unstable angina, non-Q-wave (i.e., non-ST-segment elevation) myocardial infarction, and Q-wave (i.e., ST-segment elevation) myocardial infarction.

Gene Therapy—A therapeutic regime which includes the administration of a vector containing DNA encoding a therapeutic protein, directly to affected cells where the therapeutic protein will be produced. Target tissue for gene delivery include, for example, skeletal muscle, vascular smooth muscle, and liver. Vectors include, for example, plasmid DNA, liposomes, protein-DNA conjugates, and vectors based on adenovirus or herpes virus. Gene therapy has been described, for example, by Kessler et al., PNAS, USA, 93:14082–87, 1996.

Thrombotic disorders—a disorder relating to, or affected with the formation or presence of a blood clot within a blood vessel. Such disorders include, but are not limited to, stroke, abrupt closure following angioplasty or stent placement, and thrombosis as a result of peripheral vascular surgery.

Purpura fulminans—ecchymotic skin lesions, fever, hypotension associated with bacterial sepsis, viral, bacterial or protozoan infections. Disseminated intravascular coagulation is usually present.

Tissue factor pathway inhibitor (TFPI). refers, to, naturally, or, recombinant, forms, of TFPI. This protein is believed to block tissue-mediated clotting in small blood vessels, which potentially leads to organ failure and death.

Serpin—any of a group of structurally related proteins that typically are serine protease inhibitors whose inhibiting activity is conferred by a reactive site in C highly variable and mobile peptide loop and that include but are not limited to protein C inhibitor (PCI) and $\alpha_1$-antitrypsin ($\alpha_1$-AT).

Inhibitor recognition sequence S2: the $2^{nd}$ residue N-terminal to the cleavage site of PCI or $\alpha_1$-AT.

Inhibitor recognition sequence S3': the $3^{rd}$ residue C-terminal to the cleavage site of PCI or $\alpha_1$-AT.

Inhibitor recognition sequence S4': the $4^{th}$ residue C-terminal to the cleavage site of PCI or $\alpha_1$-AT.

Wild-type protein C—the type of protein C that predominates in a natural population of humans in contrast to that of natural or laboratory mutant polypeptide forms of protein C.

Bactericidal permeability increasing protein—includes naturally and recombinantly produced bactericidal permeability increasing (BPI) protein; natural, synthetic, and recombinant biologically active polypeptide fragments of BPI protein; biologically active polypeptide variants of BPI protein or fragments thereof, including hybrid fusion proteins and dimers; biologically active variant analogs of BPI protein or fragments or variants thereof, including cysteine-substituted analogs; and BPI-derived peptides. The complete amino acid sequence of human BPI, as well as the nucleotide sequence of DNA encoding BPI have been elucidated by Gray, et al., 1989, *J. Biol. Chem* 264:9505. Recombinant genes encoding and methods for expression of BPI proteins, including BPI holoprotein and fragments of BPI are disclosed in U.S. Pat. No. 5,198,541, herein incorporated by reference.

The phrase "in combination with" as used herein, refers to the administration of additional agents with human aPC derivatives either simultaneously, sequentially or a combination thereof. Examples of additional agents are anti-platelet agents, thrombolytic agents, and BPI protein.

The amino acid abbreviations are accepted by the United States Patent and Trademark Office as set forth in 37 C.F.R. 1.822 (d)(1) (1998).

The present invention provides human protein C derivatives, which have increased anti-coagulant activity, resistance to serpin inactivation, and increased sensitivity to thrombin activation as compared to wild-type protein C and the use of these derivatives in the zymogen form as well as in the activated form. The activated form of human protein C derivatives may be produced by activating recombinant human protein C derivative zymogen in vitro or by direct secretion of the activated form of protein C. The means by which the activation occurs is not critical and the process aspects of this invention include any and all means of activation. Human protein C derivatives may be produced in eukaryotic cells, transgenic animals, or transgenic plants, including, for example, secretion from human kidney 293 cells or AV 12 cells as a zymogen, then purified and activated by techniques known to the skilled artisan.

Preferred human protein C derivatives of the present invention include S11G:Q32E:N33D:D167F:D172K:L194S, S11G:Q32E:N33D:D167F:D172K:L194S:T254S, S11G:Q32E:N33D:D167F:D172K, and H10Q:S11G:Q32E:N33D:D167F:D172K.

Human protein C derivative S11G:Q32E:N33D:D167F:D172K:L194S contains a glycine residue at position 11 instead of the serine residue normally found at this position, a glutamic acid residue at position 32 instead of the glutamine residue normally found at this position an aspartic acid residue at position 33 instead of the asparagine residue normally found at this position, a phenylalanine at position 167 rather than the aspartic acid normally found at this position, a lysine at position 172 rather than the aspartic acid normally found at this position and a serine residue at position 194 instead of the leucine residue normally found at this position. Other preferred amino acid substitutions for positions 194 include Ser, Ala, Thr, His, Leu, Lys, Arg, Asn, Asp, Glu, Gly, and Gln and any amino acid for position 11.

Human protein C derivative S11G:Q32E:N33D:D167F:D172K:L194S:T254S contains a glycine residue at position 11 instead of the serine residue normally found at this position, a glutamic acid residue at position 32 instead of the glutamine residue normally found at this position an aspartic acid residue at position 33 instead of the asparagine residue normally found at this position, a phenylalanine at position 167 rather than the aspartic acid normally found at this position, a lysine at position 172 rather than the aspartic acid normally found at this position, a serine residue at position 194 instead of the leucine residue normally found at this position, and a serine residue at position 254 instead of the threonine residue normally found at this position. Other preferred amino acid substitutions for positions 194 and 254 include Ser, Ala, Thr, His, Leu, Lys, Arg, Asn, Asp, Glu, Gly, and Gln and any amino acid for position 11.

Human protein C derivative S11G:Q32E:N33D:D167F:D172K contains a glycine residue at position 11 instead of the serine residue normally found at this position, a glutamic acid residue at position 32 instead of the glutamine residue normally found at this position an aspartic acid residue at position 33 instead of the asparagine residue normally found at this position, a phenylalanine at position 167 rather than the aspartic acid normally found at this position, and a lysine at position 172 rather than the aspartic acid normally found at this position Other preferred amino acid substitutions for positions 11 include any amino acid.

Human protein C derivative H10Q:S11G:Q32E:N33D:D167F:D172K preferably contains a glutamine at position 10 rather than the histidine residue normally found at this position, a glycine at position 11 rather than the serine normally found at this position, a glutamic acid residue at position 32 instead of the glutamine residue normally found at this position an aspartic acid residue at position 33 instead of the asparagine residue normally found at this position, a phenylalanine at position 167 rather than the aspartic acid normally found at this position, and a lysine at position 172 rather than the aspartic acid normally found at this position Other preferred amino acid substitutions for positions 11 include any amino acid.

Other embodiments of the present inventions include H10Q:S11G:S12K:D167F:D172K:L194S:T254S, S11G:Q32E:D167F:D172K:L194S, S11G:Q32E:D167F:D172K:L194S:T254S, S11G:Q32E:N33F:D167F:D172K:L194S, and S11G:Q32E:N33F:D167F:D172K:L194S:T254S, and activated forms thereof which have increased anti-coagulation activity and resistance to serpin inactivation, and increased sensitivity to thrombin activation, as compared to wild-type activated protein C.

Human protein C derivative H10Q:S11G:S12K:Dl67F:D172K:L194S:T254S preferably contains a glutamine at position 10 rather than the histidine residue normally found at this position, a glycine at position 11 rather than the serine normally found at this position, a lysine residue at position 12 rather than a serine residue normally found at this position, a phenylalanine at position 167 rather than the aspartic acid normally found at this position, a lysine at position 172 rather than the aspartic acid normally found at this position, a serine at position 194 rather than the leucine normally found at this position, and a serine at position 254 instead of a threonine normally found at this position. Other preferred amino acid substitutions for positions Other preferred amino acid substitutions for positions 194 and 254 include Ser, Ala, Thr, His, Leu, Lys, Arg, Asn, Asp, Glu, Gly, and Gln and any amino acid for positions 10, 11, and 12.

Human protein C derivative S11G:Q32E:D167F:D172K:L194S contains a glycine residue at position 11 instead of the serine residue normally found at this position, a glutamic acid residue at position 32 instead of the glutamine residue normally found at this position, a phenylalanine at position 167 rather than the aspartic acid normally found at this position, a lysine at position 172 rather than the aspartic acid normally found at this position, and a serine residue at position 194 instead of the leucine residue normally found at this position. Other preferred amino acid substitutions for positions 194 include Ser, Ala, Thr, His, Leu, Lys, Arg, Asn, Asp, Glu, Gly, and Gln and any amino acid for position 11.

Human protein C derivative S11G:Q32E:D167F:D172K:L194S:T254S contains a glycine residue at position 11 instead of the serine residue normally found at this position, a glutamic acid residue at position 32 instead of the glutamine residue normally found at this position, a phenylalanine at position 167 rather than the aspartic acid normally found at this position, a lysine at position 172 rather than the aspartic acid normally found at this position, a serine residue at position 194 instead of the leucine residue normally found at this position, and a serine residue at position 254 instead of the threonine residue normally found at this position. Other preferred amino acid substitutions for positions 194 and 254 include Ser, Ala, Thr, His, Leu, Lys, Arg, Asn, Asp, Glu, Gly, and Gln and any amino acid for position 11.

Human protein C derivative S11G:Q32E:N33F:D167F:D172K:L194S contains a glycine residue at position 11 instead of the serine residue normally found at this position, a glutamic acid residue at position 32 instead of the glutamine residue normally found at this position a phenyalanine residue at position 33 instead of the asparagine residue normally found at this position, a phenylalanine at position 167 rather than the aspartic acid normally found at this position, a lysine at position 172 rather than the aspartic acid normally found at this position, and a serine residue at position 194 instead of the leucine residue normally found at this position. Other preferred amino acid substitutions for positions 194 include Ser, Ala, Thr, His, Leu, Lys, Arg, Asn, Asp, Glu, Gly, and Gin and any amino acid for position 11.

Human protein C derivative S11G:Q32E:N33F:D167F:D172K:L194S:T254S contains a glycine residue at position 11 instead of the serine residue normally found at this position, a glutamic acid residue at position 32 instead of the glutamine residue normally found at this position a phenylalanine residue at position 33 instead of the asparagine residue normally found at this position, a phenylalanine at position 167 rather than the aspartic acid normally found at this position, a lysine at position 172 rather than the aspartic acid normally found at this position, a serine residue at position 194 instead of the leucine residue normally found at this position, and a serine residue at position 254 instead of the threonine residue normally found at this position. Other preferred amino acid substitutions for positions 194 and 254 include Ser, Ala, Thr, His, Leu, Lys, Arg, Asn, Asp, Glu, Gly, and Gln and any amino acid for position 11.

Further embodiments of the present invention include human protein C derivatives: S11G:D167F:D172K:L194S, S11G:D167F:D172K:L194S:T254S, S11G:S12K:D167F:D172K:L194S, S12K:D167F:D172K, D167F:D172K:L194S:T254S, S12K:Dl67F:D172K:L194S, S12K:D167F:D172K:L194S:T254S, Q32E:N33D:D167F:D172K, S11G:Q32E:D167F:D172K, S11G:Q32E:N33F:D167F:D172K, and activated forms thereof which have increased anti-coagulant activity, resistance to inactivation by serpins, increased sensitivity to thrombin activation or combinations of these activities as compared to wild-type human activated protein C.

Human protein C derivative S11G:D167F:D172K:L194S preferably contains a glycine residue at position 11 rather than a serine residue normally found at this position, a phenylalanine at position 167 rather than the aspartic acid normally found at this position, a lysine at position 172 rather than the aspartic acid normally found at this position, and a serine at position 194 rather than the leucine normally found at this position. Other preferred amino acid substitutions for positions 194 include Ser, Ala, Thr, His, Leu, Lys, Arg, Asn, Asp, Glu, Gly, and Gln and any amino acid for position 11.

Human protein C derivative S11G:D167F:D172K:L194S:T254S preferably contains a glycine residue at position 11 rather than a serine residue normally found at this position, a phenylalanine at position 167 rather than the aspartic acid normally found at this position, a lysine at position 172 rather than the aspartic acid normally found at this position, a serine at position 194 rather than the leucine normally found at this position, and a serine at position 254 instead of a threonine normally found at this position. Other preferred amino acid substitutions for positions 194 and 254 include Ser, Ala, Thr, His, Leu, Lys, Arg, Asn, Asp, Glu, Gly, and Gln and any amino acid for position 11.

Human protein C derivative S11G:S12K:D167F:D172K:L194S preferably contains a glycine residue at position 11 rather than a serine residue normally found at this position, a lysine residue at position 12 rather than a serine residue normally found at this position, a phenylalanine at position 167 rather than the aspartic acid normally found at this position, a lysine at position 172 rather than the aspartic acid normally found at this position, and a serine at position 194 rather than the leucine normally found at this position. Other preferred amino acid substitutions for positions 194 include Ser. Ala, Thr, His, Leu, Lys, Arg, Asn, Asp, Glu, Gly, and Gln and any amino acid for position 11 and 12.

Human protein C derivative S12K:D167F:D172K preferably contains a lysine residue at position 12 rather than a serine residue normally found at this position, a phenylalanine at position 167 rather than the aspartic acid normally found at this position, and a lysine at position 172 rather than the aspartic acid normally found at this position. Other preferred amino acid substitutions for positions 12 include any amino acid.

Human protein C derivative D167F:D172K:L194S:T254S preferably contains a phenylalanine at position 167 rather than the aspartic acid normally found at this position, a lysine at position 172 rather than the aspartic acid normally found at this position, a serine at position 194 rather than the leucine normally found at this position, and a serine at position 254 instead of a threonine normally found at this position. Other preferred amino acid substitutions for positions 194, and 254 include Ser, Ala, Thr, His, Leu, Lys, Arg, Asn, Asp, Glu, Gly, and Gln.

Human protein C derivative S12K:D167F:D172K:L194S preferably contains a lysine residue at position 12 rather than a serine residue normally found at this position, a phenylalanine at position 167 rather than the aspartic acid normally found at this position, a lysine at position 172 rather than the aspartic acid normally found at this position, and a serine at position 194 rather than the leucine normally found at this position. Other preferred amino acid substitutions for positions 194 include Ser, Ala, Thr, His, Leu, Lys, Arg, Asn, Asp, Glu, Gly, and Gln and any amino acid for position 11.

Human protein C derivative S12K:D167F:D172K:L194S:T254S preferably contains a lysine residue at position 12 rather than a serine residue normally found at this position, a phenylalanine at position 167 rather than the aspartic acid normally found at this position, a lysine at position 172 rather than the aspartic acid normally found at this position, a serine at position 194 rather than the leucine normally found at this position, and a serine at position 254 instead of a threonine normally found at this position. Other preferred amino acid substitutions for positions 194 and 254 include Ser, Ala, Thr, His, Leu, Lys, Arg, Asn, Asp, Glu, Gly, and Gln and any amino acid for position 12.

Human protein C derivative Q32E:N33D:D167F:D172K contains a glutamic acid residue at position 32 instead of the glutamine residue normally found at this position an aspartic acid residue at position 33 instead of the asparagine residue normally found at this position, a phenylalanine at position 167 rather than the aspartic acid normally found at this position, and a lysine at position 172 rather than the aspartic acid normally found at this position.

Human protein C derivative S11G:Q32E:D167F:D172K contains a glycine residue at position 11 instead of the serine residue normally found at this position, a glutamic acid residue at position 32 instead of the glutamine residue normally found at this position, a phenylalanine at position 167 rather than the aspartic acid normally found at this position, and a lysine at position 172 rather than the aspartic acid normally found at this position. Other preferred amino acid substitutions for positions 11 include any amino acid Human protein C derivative S11G:Q32E:N33F:D167F:D172K contains a glycine residue at position 11 instead of the serine residue normally found at this position, a glutamic acid residue at position 32 instead of the glutamine residue normally found at this position a phenylalanine residue at position 33 instead of the asparagine residue normally found at this position, a phenylalanine at position 167 rather than the aspartic acid normally found at this position, and a lysine at position 172 rather than the aspartic acid normally found at this position. Other preferred amino acid substitutions for position 11 include any amino acid.

In addition, human protein C derivatives of the present invention include additional deletions, additions, or substitutions of amino acid residues of the protein C derivatives described above, but which result in changes that do not effect the basic characteristics of this invention. Amino acid substitutions may be made on the basis of similarity in polarity, charge, solubility, hydrophobicity, hydrophilicity, and/or the amphipathic nature of the residues involved. Thus, the derivatives of the present invention include derivatives having an amino acid sequence that vary from SEQ ID NOS: 3, 4, 5, and 6, by conservative substitutions i.e., those that substitute a residue with another of like characteristics. Typical substitutions are among Ala, Val, Leu and Ile; among Ser and Thr; among the acidic residues Asp and Glu; among Asn and Gln; and among the basic residues Lys and Arg; or aromatic residues Phe and Tyr. Other derivatives are those in which several, 5–10, 1–5, or 1–2 amino acids are substituted, deleted, or added in any combination. A preferred embodiment is based on SEQ ID NO: 1 includes the addition of the 42 amino acid signal peptide sequence as illustrated in FIG. 1 and shown in SEQ ID NO: 2.

Preferably, the human protein C derivatives of the present invention are not further substituted or modified. That is, substitutions are limited to the derivatives of the present invention.

The invention also provides DNA compounds for use in making the human protein C derivatives. These DNA compounds comprise the coding sequence for the light chain of human protein C zymogen or human protein C derivative zymogen positioned immediately adjacent to, downstream of, and in translational reading frame with the prepropeptide sequence of human protein C zymogen or human protein C derivative zymogen. The DNA sequences preferably encode the Lys-Arg dipeptide which is processed during maturation of the protein C molecule, the activation peptide and the heavy chain of the human protein C derivative. Thus, the human protein C derivatives of the present invention are variant or mutant polypeptides which contain at least 3, preferably 3 to 7 amino acids, which differ from the wild-type protein C sequence identified as SEQ ID NO: 1 (which does not contain the 42 amino acid signal sequence) or the corresponding wild-type amino acid in SEQ ID NO: 2 (which contains the 42 amino acid signal sequence). Thus, one skilled in the art recognizes that a human protein C derivative which differs from the amino acid sequence of the wild-type protein C sequence identified as SEQ ID NO: 1 inherently corresponds to the wild-type protein C sequence identified as SEQ ID NO: 2 at the amino acid position determined after removal of the 42 amino acid signal sequence. Furthermore, one skilled in the art recognizes that prior to activation, the cleavage of the lysine and arginine residues (positions 156 and 157) occurs.

Those skilled in the art will recognize that, due to the degeneracy of the genetic code, a variety of DNA compounds can encode the derivatives described above. U.S. Pat. No. 4,775,624, the entire teaching of which is herein incorporated by reference, discloses the wild-type form of the human protein C molecule. The skilled artisan could readily determine which changes in the DNA sequences which could encode the exact derivatives as disclosed herein. The invention is not limited to the specific DNA sequences disclosed. Consequently, the construction described below and in the accompanying Examples for the preferred DNA compounds are merely illustrative and do not limit the scope of the invention.

All of the DNA compounds of the present invention were prepared by the use of site-directed mutagenesis to change particular positions within the human protein C zymogen. The technique for modifying nucleotide sequences by site-directed mutagenesis is well known to those skilled in the art. See e.g., Sambrook, Fritsch & Maniatis, Molecular Cloning: *A Laboratory Manual*, second Edition (1989).

The human protein C derivatives can be made by techniques well known in the art utilizing eukaryotic cell lines, transgenic animals, or transgenic plants. Skilled artisans will readily understand that appropriate host eukaryotic cell lines include but are not limited to HepG2, LLC-$MK_2$, CHO-K1, 293, or AV12 cells, examples of which are described in U.S. Pat. No. 5,681,932, herein incorporated by reference. Furthermore, examples of transgenic production of recombinant proteins are described in U.S. Pat. Nos. 5,589,604 and 5,650,503, herein incorporated by reference.

Skilled artisans recognize that a variety of vectors are useful in the expression of a DNA sequence of interest in a eukaryotic host cell. Vectors that are suitable for expression in mammalian cells include, but are not limited to: pGT-h, pGT-d; pCDNA 3.0, pCDNA 3.1, pCDNA 3.1+Zeo, and pCDNA 3.1+Hygro (Invitrogen); and, pIRES/Hygro, and pIRES/neo (Clonetech). The preferred vector of the present invention is pIG3 as described in Example 1.

Other sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e. to maintain the proper reading frame.

The human protein C derivatives made by any of these methods must undergo post-translational modifications such as the addition of nine or ten gamma-carboxy-glutamates, the addition of one erythro-beta-hydroxy-Asp (beta-hydroxylation), the addition of four Asn-linked oligosaccharides (glycosylation) and, the removal of the leader sequence (42 amino acid residues). Such post-translational modifications are necessary for efficient production and secretion of the protein C derivatives from mammalian cells.

It is known in the art that post-translational modifications of recombinant proteins such as the human protein C derivatives of the present invention may vary depending on which host cell line is utilized for the expression of the recombinant protein. For example, the post-translational modification of gamma-carboxylation, which is essential for the anti-coagulant activity of the human protein C derivatives of the present invention, may be higher, slightly lower, or much lower than plasma derived wild-type protein C gamma-carboxylation, depending on the host cell line used (Yan et al., *Bio/Technology* 8(7):655–661, 1990). Such differences in gamma-carboxylation provide a basis for the use of site-directed mutagenesis to change particular positions within the human protein C molecule that will result in an increase in anti-coagulant activity.

The human protein C derivatives of the present invention may be administered as a zymogen or in the activated form. Methods for the activation of zymogen forms of human protein C and human protein C derivatives to activated human protein C and activated human protein C derivatives are old and well known in the art. Human protein C may be activated by thrombin alone, by a thrombin/thrombomodulin complex, by RVV-X, a protease from Russell's Viper venom, by pancreatic trypsin or by other proteolytic enzymes.

The present invention further provides for the treatment of acute coronary syndromes comprising myocardial infarction, and unstable angina with human protein C derivatives with increased anti-coagulation activity, resistance to serpin inactivation, and increased sensitivity to thrombin activation as compared to wild-type aPC.

The recombinant human protein C derivatives of the present invention are also useful for the treatment of thrombotic disorders such as stroke, abrupt closure following angioplasty or stent placement, and thrombosis as a result of peripheral vascular surgery.

Additionally, the recombinant human protein C derivatives of the present invention are useful for the treatment of vascular occlusive disorders or hypercoagulable states associated with sepsis, disseminated intravascular coagulation, major trauma, major surgery, burns, adult respiratory distress syndrome, transplantations, deep vein thrombosis, heparin-induced thrombocytopenia, sickle cell disease, thalassemia, viral hemorrhagic fever, thrombotic thrombocytopenic purpura, and hemolytic uremic syndrome. In another embodiment, the recombinant human protein C derivatives of the present invention are useful for the treatment of sepsis in combination with bacterial permeability increasing protein. In yet another aspect of this invention the activated human protein C derivatives of the present invention are combined with an anti-platelet agent(s) to treat or prevent various disorders, such as, thrombotic disease.

In another embodiment, the recombinant human protein C derivatives of the present invention are useful for the treatment of sepsis in combination with tissue factor pathway inhibitor.

Another aspect of the invention comprises treating the diseases and conditions caused or resulting from protein C deficiency as defined herein. This aspect of the invention contemplates any and all modifications to any aPC molecule resulting in increased anti-coagulant activity and resistance to serpin inactivation as compared to wild-type aPC.

The recombinant human protein C derivatives of the present invention are useful for the treatment of acute arterial thrombotic occlusion, thromboembolism, or stenosis in coronary, cerebral or peripheral arteries or in vascular grafts, in combination with a thrombolytic agent such as tissue plasminogen activator, streptokinase, and related compounds or analogs thereof.

The human protein C derivatives can be formulated according to known methods to prepare a pharmaceutical composition comprising as the active agent an aPC derivative and a pharmaceutically acceptable bulking agent. For example, a desired formulation would be one that is a stable lyophilized product of high purity comprising a bulking agent such as sucrose, trehalose or raffinose; a salt such as sodium chloride or potassium chloride; a buffer such as sodium citrate, Tris acetate, or sodium phosphate, at a pH of about 5.5 to about 6.5; and an activated human protein C derivative.

The human aPC derivatives of the present invention can be administered at an appropriate dose level understood and appreciated in the art and determined by the attending physician evaluating the particular circumstances surrounding the case. Preferably, the amount of human aPC derivative administered will be from about 0.01 μg/kg/hr to about 50 μg/kg/hr. More preferably, the amount of human aPC derivative administered will be about 0.1 μg/kg/hr to about 25 μg/kg/hr. Yet even more preferably the amount of human aPC derivative administered will be about 0.1 μg/kg/hr to about 15 μg/kg/hr. Even more preferably the amount of human aPC derivative administered will be about 1 μg/kg/hr to about 15 μg/kg/hr. The most preferable amounts of human aPC derivative administered will be about 5 μg/kg/hr or about 10 μg/kg/hr.

Preferably, the human aPC derivatives will be administered parenterally to ensure delivery into the bloodstream in an effective form by injecting a dose of 0.01 mg/kg/day to about 1.0 mg/kg/day, one to six times a day, for one to ten days. More preferably, the human aPC derivatives will be administered B.I.D. (2 times a day) for three days.

Alternatively, the human aPC derivatives will be administered at a dose of about 0.01 μug/kg/hr to about 50 μg/kg/hr, by continuous infusion for 1 to 240 hours.

The preferred plasma ranges obtained from the amount of human protein C derivative administered will be 0.02 ng/ml to less than 100 ng/ml.

In another alternative, the human protein C derivatives will be administered by injecting a portion (⅓ to ½) of the appropriate dose per hour as a bolus injection over a time from about 5 minutes to about 120 minutes, followed by continuous infusion of the appropriate dose for up to 240 hours.

In another alternative, the human protein C derivatives will be administered by local delivery through an intracoronary catheter as an adjunct to high-risk angioplasty (with and without stenting, and with or without combination therapy with anti-platelet agents). The amount of human protein C derivative administered will be from about 0.01 mg/kg/day to about 1.0 mg/kg/day by continuous infusion, bolus injection, or a combination thereof.

In another alternative, the human protein C derivatives will be administered subcutaneously at a dose of 0.01 mg/kg/day to about 10.0 mg/kg/day, to ensure a slower release into the bloodstream. Formulation for subcutaneous preparations will be done using known methods to prepare such pharmaceutical compositions.

The human protein C derivatives described in this invention have increased anti-coagulant activity, resistance to serpin inactivation, and increased sensitivity to thrombin activation. Therefore, these compounds provide various advantages over conventional therapeutic agents, for example, site-activation, less frequent administration and/or smaller dosages, increased efficacy, and thus a reduction in the overall cost of production of the therapy.

The following Examples are provided merely to further illustrate the present invention. The scope of the invention shall not be construed as merely consisting of the following Examples.

EXAMPLE 1

Protein C Derivative Construction and Production

Human protein C derivatives were constructed using the polymerase chain reaction (PCR) following standard methods. The source of the wild-type coding sequence was plasmid pLPC (*Bio/Technology* 5:1189–1192, 1987). The universal PCR primers used include: PC001b; 5'GCGATG <u>TCTAGA</u>ccaccATGTGGCAGCTCACAAGCCTCCTGC-3', which encodes for an XbaI restriction site (underlined) used-for subcloning, a Kozak consensus sequence (lowercase) (Kozak, *J Cell Biol* 108(2):229–41, 1989), and the 5' end of the coding region for protein C: PC002e; 5'-CAGGGA<u>TGATCA</u>CTAAGGTGCCCAGCTCTTC-TGG-3', which encodes for the 3' end of the coding region for human protein C, and includes a BclI restriction site (underlined) for subcloning. All site-directed mutagenesis was accomplished by established PCR methodology, using complementary oligonucleotides containing the desired sequence changes. The first round of PCR was used to amplify two fragments of the protein C gene; the 5' fragment was generated using PC001b and the antisense mutagenic primer, and the 3' fragment was generated using PC002e and the sense mutagenic primer. The resulting amplified products were purified by standard procedures. These fragments were combined and then used as a template for a second round of PCR using primers PC001b and PC002e. The final PCR product was digested with XbaI and BclI and subcloned into similarly digested expression vector pIG3. A wild-type construct was similarly generated by PCR using the two universal primers and the plasmid pLPC as the template, followed by subcloning into pIG3. The mutations were confirmed by DNA sequencing of both the coding and non-coding strands. The pIG3 vector was generated by the insertion of an "internal ribosome entry site" (IRES) (Jackson, et al., *Trends Biochem Sci* 15(12):447–83, 1990) and green fluorescent protein (GFP) (Cormack, et al., *Gene* 173:33–38, 1996) gene into the mammalian expression vector pGTD (Gerlitz, et al., *Biochem J* 295(Pt 1):131–40, 1993). When a cDNA of interest is cloned into the multiple cloning site of pIG3, the GBMT promoter (Berg, et al., *Nucleic Acids Res* 20(20):5485–6, 1992) drives expression of a bicistronic mRNA (5'-cDNA-IRES-GFP-3'). Efficient translation of the first cistron is initiated by classical assembly of ribosome subunits on the 5'-methylated cap structure of the mRNA; while the normally inefficient translation of a second cistron is overcome by the IRES sequence which allows for internal ribosome assembly on the mRNA. The coupling of the cDNA and reporter on a single mRNA, translated as separate proteins, allows one to screen for the highest-producing clones on the basis of fluorescence intensity. The expression vector also contains an ampicillin resistance cassette for maintenance of the plasmid in *E. coli*, and a murine DHFR gene with appropriate expression sequences for selection and amplification purposes in mammalian tissue expression.

The adenovirus-transformed Syrian hamster AV12–664 cell line was grown in Dulbecco's modified Eagle's medium supplemented with 10% fetal bovine serum, 50 μg/mL gentamicin, 200 μg/mL Geneticin (G418), and 10 μg/mL vitamin K1. One day prior to transfection, cells were plated at a density of about $10^5$ cells/25 $cm^2$. FspI-linearized plasmids were transfected using either the calcium phosphate method (ProFection, Gibco BRL-Life Technologies) or FuGene-6 (Boehringer Mannheim), following the manufacturer's instructions. Approximately 48 hours after transfection, the medium was replaced with medium containing 250 nM methotrexate for selection. Colonies resistant to methotrexate were pooled 2–3 weeks after applying drug selection and expanded. The pools were subjected to fluorescence activated cell sorting based upon GFP fluorescence intensity (Cormack, 1996), with the most intense 5% of fluorescent cells being retained and expanded. To obtain material for purification, recombinant cells were grown in a modified mixture of Dulbecco's modified Eagle's and Ham's F-12 media (1:3) containing 1 μg/mL human insulin, 1 μg/mL human transferrin, and 10 μg/mL vitamin K1. Conditioned media were collected, adjusted to a final concentration of 5 mM benzamidine and 5 mM EDTA, pH 8.0, and protein C was purified via anion-exchange chromatography as described (Yan, et al., *Bio/Technology* 8:655–661, 1990). Purified protein was desalted/concentrated in Ultrafree-CL 30,000 NMWL filtration units (Millipore) using Buffer A (150 mM NaCl, 20 mM Tris-HCl, pH 7.4), and quantitated by Pierce BCA assay using bovine serum albumin (BSA) as the standard.

EXAMPLE 2

Serpin Resistant Mutants

The use of site-directed mutagenesis to change particular positions within human protein C molecule that decrease inactivation by serpins, and consequently result in extended plasma half-lives is described. The recognition sequences in the two primary aPC inhibitors $\alpha_1$-AT and PCI reveal some differences that can be exploited by altering the residues in aPC that interact with these sequences. Table 1 depicts the sequences recognized by aPC. The cleavage site occurs between the two residues shown in italics. Residues occupying the specific subsites, S2, S3', and S4', are underlined.

In general, the recognized sites in factor Va are different from the sites in either factor VIIIa or the inhibitors, therefore, it is possible to engineer the active site of aPC to preferentially cleave the more critical coagulant factor Va, while at the same time decrease aPC's likelihood of being inhibited by serpins.

TABLE I

| Coagulation Factors | S2 ... S3.S4. | S2 ...S3.S4. | |
|---|---|---|---|
| Factor Va | 300–313 | N C P K K T *R* | *N* L K K I T R |
| Factor Va | 500–513 | S R S L D R *R* | *G* I Q R A A A |
| Factor Va | 673–685 | S T V M A T *R* | *K* M H D R L E |
| Factor Villa | 330–341 | P E E P Q L *R* | *M* K N N E E A |
| Factor Villa | 560–571 | K E S V D Q *R* | *G* N Q I M S D |
| Serpins | | | |
| PCI | | G T I F T F *R* | *S* A R L N S Q |
| $\alpha_1$-AT | | F L E A I P *M* | *S* I P P E V K |

In particular, three sites of recognition within the active site show distinctive differences between substrate recognition sequences and inhibitor recognition sequences: S2 (the $2^{nd}$ residue N-terminal to the cleavage site), S3' site, and S4'. The S2 site is primarily occupied by polar residues in the factor Va sequences; unlike PCI and $\alpha_1$-AT, which have hydrophobic residues at this position. The S3' site occupied by polar side chains in all of the substrate sequences, but notably, a hydrophobic side chain in the $\alpha_1$-AT sequence. The S4' site is occupied by charged residues in all three factor Va sequences, but is occupied by hydrophobic residues in the factor VIIIa and inhibitor sequences.

Based upon the crystal structures of the PPACK-inibited aPC (Mather, et al., *EMBO J.* 15(24):6822–6831, 1996) and Hirulog 3-inhibited thrombin (Qiu, et al., *Biochemistry* 31(47):11689–97, 1992), two aPC-substrate model structures were created and energy minimized using a CHARMm protocol:

(1) The sequence representing the factor Va R506 cleavage sequence.

(2) The recognition sequence of $\alpha_1$-AT, with the Met substituted with Arg (corresponding to a polypeptide of $\alpha_1$-AT which exhibits extremely high affinity for aPC).

These models allowed for the identification of residues which form critical contacts in these three specific sites. A summary of residues which may form specific contacts within the active site, and replacements that are expected to provide enhanced specificity and/or activity are summarized in Table II. In general, mutations of residues that form contacts within the specific subsites of the active site are designed to reflect changes in the environment to drive the specificity of human protein C derivatives away from the recognition of the two primary physiological inhibitors, and potentially enhance human protein C derivative's proteolytic activity.

TABLE II

| | Mutations constructed for alteration of specificity | | |
|---|---|---|---|
| Site | aPC Residue | Constructed replacements | Substrate Contact |
| S2 | Thr254 | Ser | Aliphatic part of sidechain |
| S3' | Tyr302 | Glu, Gln | End of sidechain |
| S4' | Leu194 | Ser, Thr, Ala | Aliphatic part of sidechain |
| S4' | Ala195 | Gly | Aliphatic part of sidechain |
| S4' | Leu228 | Gln | End of sidechain |
| S4' | Phe316 | Asn | Aliphatic part of sidechain |

EXAMPLE 3

Activation of Recombinant Protein C

Complete activation of the zymogen forms of protein C and derivatives was accomplished by incubation with thrombin-sepharose. Thrombin-sepharose was washed extensively with Buffer A. 200 μL of packed thrombin-sepharose was mixed with 250 μg of protein C in 1 mL of the same buffer and incubated at 37° C. for 4 hours with gentle shaking on a rotating platform. During the course of the incubation, the degree of protein C activation was monitored by briefly pelleting the thrombin-sepharose, and assaying a small aliquot of the supernatant for aPC activity using the chromogenic substrate S-2366 (DiaPharma). Following complete activation, the thrombin-sepharose was pelleted, and the supernatant collected. aPC concentration was verified by Pierce BCA assay, and the aPC was either assayed directly, or frozen in aliquots at −80° C. All derivatives were analyzed by SDS-PAGE with either Coomassie-blue staining or Western Blot analysis to confirm complete activation (Laemmli, *Nature* 227:680–685, 1970).

EXAMPLE 4

Functional Characterization

The amidolytic activity of recombinant human protein C derivatives were determined by hydrolysis of the tri-peptide substrates S-2366 (Glu-Pro-Arg-p-nitroanilide), S-2238 (Pip-Pro-Arg-p-nitroanilide), and S-2288 (Ile-Pro-Arg-p-nitroanilide). The anti-coagulant activity is shown as measured clotting time in an aPTT at 500 ng $mL^{-1}$ aPC. Amidolytic activities were measured using the chromogenic substrate S-2366.

Assays were performed at 25° C., in Buffer A containing 1 mg $mL^{-1}$ BSA, 3 mM $CaCl_2$, and 0.5 nM aPC. Reactions (200 μL/well) were performed in a 96-well microtiter plate, and amidolytic activity was measured as the change in absorbance units/min at 405 nm as monitored in a ThermoMax kinetic micrometer plate reader. Kinetic constants were derived by fitting velocity data at varying substrate concentrations (16 μM to 2 μM) to the Michaelis-Menten equation. Changes in $A_{405}$ were converted to mmol product using a path length of 0.53 cm (Molecular Devices Technical Applications Bulletin 4-1), and an extinction coefficient for the released p-nitroanilide of 9620 $M^{-1}$ $cm^{-1}$ (Pfleiderer, *Methods Enzymol* 19:514–521, 1970). Anti-coagulant activity was assessed by measuring the prolongation of clotting time in the activated partial thromboplastin time clotting assay (Helena Laboratories). Clotting reactions were monitored in a ThermoMax kinetic microtiter plate reader, measuring the time to $V_{max}$ in the change in turbidity.

We claim:

1. A human protein C derivative comprising SEQ ID NO: 1 wherein,

Asp at position 167 is substituted with Phe,

Asp at position 172 is substituted with Lys, and further comprising at least one amino acid substitution selected from the group consisting of:

(a) His at position 10, Ser at position 11, or Ser at position 12 are independently substituted with any amino acid, (b) Gin at position 32 is substituted with Glu, (c) Asn at position 33 is substituted with Asp or Phe, and (d) amino acids at positions 194, 195, 228, 249, 254, 302, or 316 are substituted with an amino acid selected from Ser, Ala, Thr, His, Leu, Lys, Arg, Asn, Asp, Glu, Gly, and Gln.

2. The human protein C derivative of claim 1, wherein said human protein C derivative is in its activated form.

3. The human protein C derivative of claim 2 where the derivative is selected from the group consisting of: S11G:Q32E:N33D:D167F:D172K:L194S(SEQ ID NO: 3); S11G:Q32E:N33D:D167F:D172K:L194S:T254S(SEQ ID NO: 4); S11G:Q32E:N33D:D167F:D172K(SEQ ID NO: 5); or H10Q:S11G:Q32E:N33D:D167F:D172K (SEQ ID NO: 6).

4. A recombinant DNA molecule encoding the human protein C derivative of claim 1.

5. A recombinant DNA molecule encoding the human protein C derivative of claim 2.

6. A recombinant DNA molecule encoding the human protein C derivative of claim 3.

7. A method of treating acute coronary syndromes and disease states predisposing to thrombosis, vascular occlusive disorders and hypercoagulable states, or protein C deficiency which comprises: administering to a patient in need thereof a pharmaceutically effective amount of the human protein C derivative of claim 2.

8. The method of claim 7 wherein said human protein C derivative is selected from the group consisting of: S11G:Q32E:N33D:D167F:D172K:L194S (SEQ ID NO: 3); S11G:Q32E:N33D:D167F:D172K:L194S:T254S (SEQ ID NO: 4); S11G:Q32E:N33D:D167F:D172K (SEQ ID NO: 5); or H10Q:S11G:Q32E:N33D:D167F:D172K (SEQ ID NO: 6).

9. A pharmaceutical composition comprising the human protein C derivative of claim 1 in a pharmaceutically acceptable diluent.

10. A pharmaceutical composition comprising the human protein C derivative of claim 2 a pharmaceutically acceptable diluent.

11. A pharmaceutical composition comprising the human protein C derivative of claim 3 in a pharmaceutically acceptable diluent.

12. A vector comprising a nucleic acid according to claim 4.

13. A vector comprising a nucleic acid according to claim 5.

14. A vector comprising a nucleic acid according to claim 6.

15. A host cell transformed by the vector according to claim 12.

16. A host cell transformed by the vector according to claim 13.

17. A host cell transformed by the vector according to claim 14.

18. A method of producing an activated human protein C derivative comprising (i) transforming a host cell with a vector containing a nucleic acid encoding a human protein C derivative comprising SEQ ID NO: 1 wherein, Asp at position 167 is substituted with Phe, Asp at position 172 is substituted with Lys, and further comprising at least one amino acid substitution selected from the group consisting of of:

(a) His at position 10, Ser at position 11, or Ser at position 12 are independently substituted with any amino acid, (b) Gin at position 32 is substituted with Glu, (c) Asn at position 33 is substituted with Asp or Phe, and (d) amino acids at positions 194, 195, 228, 249, 254, 302, or 316 are substituted with an amino acid selected from Ser, Ala, Thr, His, Leu, Lys, Arg, Asn, Asp, Glu, Gly, and Gin;

(ii) culturing said host cell in a medium appropriate for expression of said human protein C derivative;

(iii) isolating said human protein C derivative from the culture medium; and (iv) activating said human protein C derivative.

* * * * *